United States Patent [19]

Bronner

[11] 4,027,670

[45] June 7, 1977

[54] CONTRACEPTIVE DEVICE

[76] Inventor: Emanuel H. Bronner, Box 28, Escondido, Calif. 92025

[22] Filed: Oct. 15, 1976

[21] Appl. No.: 732,800

[52] U.S. Cl. .............................. 128/261; 128/260; 222/107; 206/438; 424/14

[51] Int. Cl.² ........................................ A61M 31/00

[58] Field of Search .......... 128/260, 261, 271, 232; 424/14, 34, 37, 38; 220/DIG. 31; 222/107, 541; 206/438, 446, 498

[56] References Cited

UNITED STATES PATENTS

| | | | |
|---|---|---|---|
| 2,129,627 | 9/1938 | Sands et al. | 128/271 |
| 2,281,473 | 4/1942 | Brewer | 206/438 |
| 2,510,249 | 6/1950 | Penska | 128/294 |
| 2,792,149 | 5/1957 | Lutz | 222/107 |
| 2,857,914 | 10/1958 | Carliner | 128/261 X |
| 3,092,251 | 6/1963 | Jaggers | 206/438 X |
| 3,303,847 | 2/1967 | Eaton | 128/261 X |
| 3,601,252 | 8/1971 | Sager | 206/498 |
| 3,664,341 | 5/1972 | Gordon | 424/14 X |
| 3,876,757 | 4/1975 | Sherm | 128/271 X |
| 3,886,940 | 6/1975 | Squibb | 128/271 |
| 3,901,233 | 8/1975 | Grossan | 128/261 |

FOREIGN PATENTS OR APPLICATIONS 475,988  11/1937  United Kingdom

*Primary Examiner*—Aldrich F. Medbery
*Attorney, Agent, or Firm*—Brown & Martin

[57] ABSTRACT

A contraceptive device containing a contraceptive gel for insertion into the vagina. The gel is made of natural ingredients and has a pH of approximately 2. The gel includes citric acid for providing the low pH; glycerine which acts as an emollient lubricant, and an emulsifier; aromatic malic acid, which acts as a stabilizer and an aromatic deodorant; kelco and/or wood celulose, which keeps the gel from liquifying at high temperatures; and distilled water.

The contraceptive device includes a delicate elongated inside sausage casing containing the gel, and having a closed insertion end that will open to release the gel when the inside casing is squeezed; a lubricant covering the outside of the inside casing at the insertion end; a semi-sausage casing covering the lubricated insertion end of the inside casing for maintaining the lubricant in a lubricant state and at the insertion end, the semi-sausage casing having a closed end fitted over the lubricated insertion end of the inside casing and an open end fitted over the inside casing near the longitudinal mid-portion of the inside casing; and a tear strip having a first length removably attached to the open end of the semi-sausage casing and to the inside casing for hygenically sealing the lubricated insertion end of the inside casing and a second length attached to the semi-sausage casing to enable removal of the semi-sausage casing for exposing the lubricated insertion end of the inside sausage casing.

19 Claims, 6 Drawing Figures

CONTRACEPTIVE DEVICE

BACKGROUND OF THE INVENTION

The present invention generally pertains to contraceptive devices and is particularly directed to contraceptive devices containing a contraceptive gel for insertion into the vagina.

In view of the rapidly expanding rate of growth of the world's population, there is a great need for improvement in contraceptive devices. The "pill" has proven unsatisfactory in many cases because of harmful side effects, as have intra-uterine devices. Other means of preventing contraception, such as the "rhythm method" and the use of condoms have not been reliable.

There is, however, a reliable and safe method of preventing conception. According to God's natural law, conception is impossible when the pH within the vagina is less than 4.0. Consistent with this law of nature, the Essenes over 2,000 years ago prescribed as a method of contraception the placement of a rose hip in the vagina during intercourse, the rose hip being rich in ascorbic acid and having the effect of lowering the pH within the vagina sufficiently to prevent conception. It is also known that a lemon slice may be inserted into the vagina during intercourse to lower the pH in order to prevent conception.

This method of contraception has not been widely accepted, however. The use of rose hips and lemon slices is neither practical nor convenient.

There has been one known contraceptive device based on this natural law. This device is a suppository type device containing a concentrated synthetic chemical formulation (such as boric acid, alum, thymol, monochlorothymol, phenylmercuric borate and aromatics, for example) for lowering the pH to less than 4.0. This formulation is carried by hardened cocoa butter in a bullet-shaped suppository and is spread within the vagina when the cocoa butter melts, a process requiring a wait of a few minutes after the suppository is inserted. This contraceptive device has not proven fully satisfactory in view of such a wait. Also, because of the nature of the synthetic chemical formulation, it can be applied in only a relatively small dosage of not more than about 3 grams, thus limiting the duration over which it is effective for preventing conception.

It is the object of the present invention to provide an inexpensive contraceptive device that can be used quickly in a convenient uncomplicated manner and also a reliable, safe and an inexpensive contraceptive gel of natural, harmless ingredients that may be used in such a contraceptive device.

SUMMARY OF THE INVENTION

The contraceptive device, of the present invention includes a contraceptive gel having a pH of less than 3.0; a delicate elongated inside sausage casing containing the gel, and having a closed insertion end that will open to release the gel when the inside casing is squeezed; a lubricant covering the outside of the inside casing at the insertion end; a semi-sausage casing covering the lubricated insertion end of the inside casing for maintaining the lubricant in a lubricant state and at the insertion end, the semi-sausage casing having a closed end fitted over the lubricated insertion end of the inside casing and an open end fitted over the inside casing near the mid-portion of the inside casing; and a tear strip having a first length removably attached to the open end of the semi-saucage casing and to the inside casing for hygenically sealing the lubricated insertion end of the inside casing and a second length attached to the semi-sausage casing to enable removal of the semi-sausage casing for exposing the lubricated insertion end of the inside sausage casing.

The contraceptive gel of the present invention consists of natural, edible, non-irritating, harmless ingredients including an acid for lowering the pH within the vagina to less than 4.0; an emollient lubricant; an emulsifier; a substance for stablizing the gel; an aromatic deodorant; a substance, such as kelco and/or wood celulose, for keeping the gel from liquefying at higher than ambient temperatures; and distilled water. In a preferred embodiment, the gel has the following approximate proportions of such ingredients; 2 percent citric acid for lowering the pH of the vagina, 5 percent glycerine for providing the emollient lubricant the emulsifier; 1 percent aromatic malic acid for stabilizing the gel and for providing the aromatic deodorant; 2 percent kelco and/or wood celulose; and 90 percent distilled water. A contraceptive gel of such proportions has a stable pH of less than 3.0.

The inclusion of sausage casings in the contraceptive device provides a component that may be readily and economically manufactured with existing technology so as to provide a contraceptive device that is sufficiently inexpensive that its cost will not pose a deterrent to its acquisition and use. Also sausage casings, typically being made from methyl celulose, are biodegradable and disposable.

The ingredients used in the preferred embodiment of the contraceptive gel are relatively inexpensive and also are biodegradable. Further, they are natural, edible, non-irritating ingredients that may safely be deposited in the vagina without harmful effect.

DESCRIPTION OF THE PREFERRED EMBODIMENT

The contraceptive gel is manufactured from edible, natural, non-irritating, harmless ingredients that are biodegradable, In the preferred embodiment, the ingredients are mixed in the following proportions: 90 percent distilled water; 2 percent citric acid; 5 percent glycerine; 1 percent aromatic malic acid and 2 percent kelco and/or wood celulose. The citric acid is derived from lemons, the glycerine from coconut oil, the malic acid from apples, the kelco from ocean kelp or dulse, and the wood celulose from wood pulp. Some other edible acid, such as a aromatic acetic acid (which is red grape vinegar) may be substituted for the citric acid.

Figure 1:
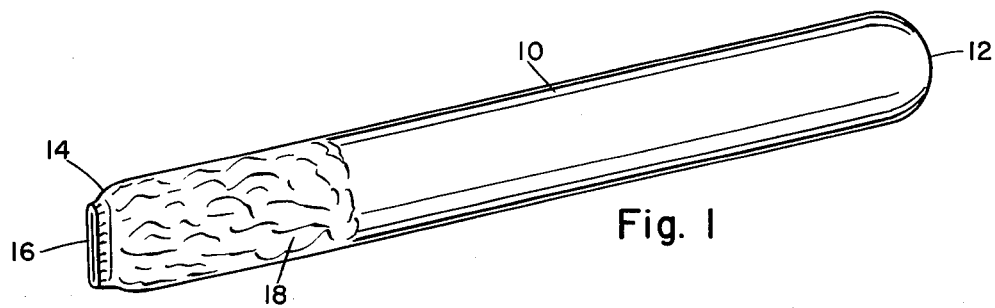
FIG. 1 is a perspective view of the inside sausage casing containing the contraceptive gel and having a lubricant covering its insertion end.
Figure 2:
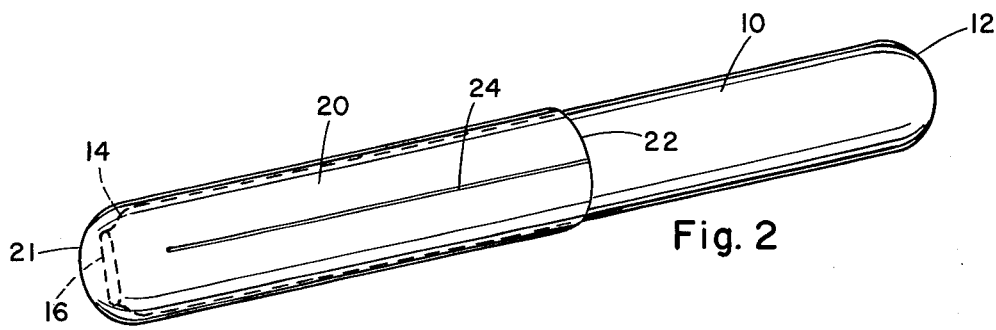
FIG. 2 is a perspective view showing the semi-sausage casing covering the insertion end of the inside casing.

Referring to FIG. 1, the contraceptive gel 8 (see FIG. 4) is contained in a delicate elongated inside sausage casing 10. The size of the inside casing 10 is dependent upon the quantity of contraceptive gel 8 to be enclosed therein, with 1 ounce (28 grams), 2 ounce (56 grams) and 3 ounce (85 grams) size containers being preferred. The larger sizes provide longer lasting protection against conception. It has been determined that 1 ounce of gel having a pH of about 2.0 to 2.3 will maintain the pH within the vagina safely below 4.0 until after approximately 10 orgasms, or after the insertion of approximately 10 ounces of semen. This degree of protection is significantly longer than with the prior art suppository type contraceptive which is limited to relatively smaller insertion dosages because of the nature of its synthetic chemical formulation, which in large amounts would become irritating.

The inside casing is preferably about 6 inches (15 cm) long so that it may be easily gripped at the end 12 when the insertion end 14 is inserted into the vagina. The end 12 is rounded and permanently sealed upon manufacture of the inside casing 10. The insertion end 14 has an envelope-shaped closure 16 which is not sealed until after the contraceptive gel has been placed within the inside casing 10. The closure 16 will open to release the gel when the inside casing 10 is squeezed.

A lubricant 18, such as petroleum jelly is applied over approximately 25 percent of the inside casing 10 at the insertion end 14 thereof.

A semi-sausage casing 20 is fitted over the insertion end 14 of the inside casing 10 to cover the lubricant 18. The semi-sausage casing 20 has a closed end 21 fitted over the lubricated insertion end 14 of the inside casing 10 and an open end 22 fitted over the inside casing 10 near the longitudinal mid-portion of the inside casing 10. The semi-sausage casing 20 is weakened along an indentation 24 extending longitudinally from the opening end 22 to an area 26 near its closed end 21.

Figures 3, 4:
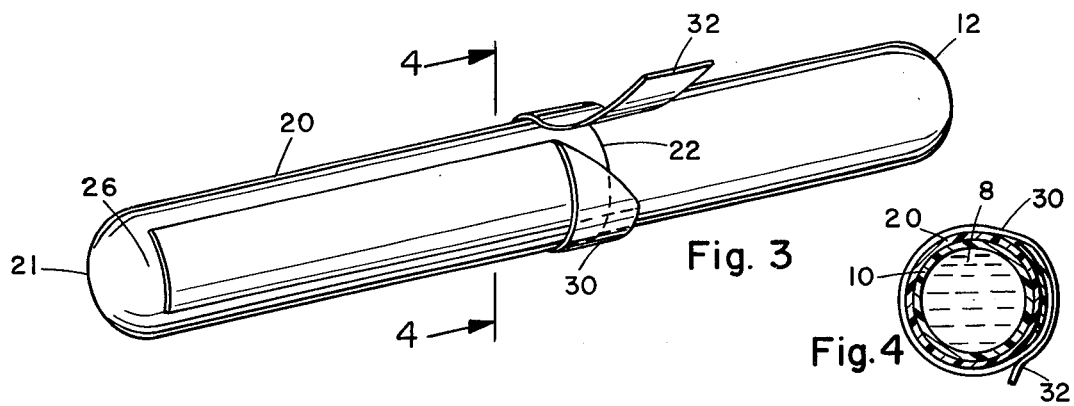
FIG. 3 is a perspective view showing how the tear strip is applied to hygenically seal the lubricated insertion end of the inside casing and also to enable removal of the semi-sausage casing.
FIG. 4 is a sectional view taken on line 4—4 of FIG. 3 with the tear strip closed to complete the seal.

Referring now to FIG. 3, a tear strip 30 is securely attached with glue to the semi-sausage casing 20 near the open end 21 of the semi-sausage case 20 in the area 26 and is extended over the indentation 24 to the open end 22 of the semi-sausage casing 20, where it is folded over at 90° and wrapped around the inside casing 10 and the semi-sausage casing 20 to hygenically seal the lubricated insertion end 14 of the inside casing 10.

Between the open end 22 and the area 26 of the semi-sausage casing 20 the tear strip is removably attached to the semi-sausage casing 20 but nevertheless so attached that the semi-sausage casing 20 will separate at the indentation 24 when the tear strip 30 is pulled from the open end 22 toward the closed end 21 of the semi-sausage casing 20. The removable attachment of the tear strip to the inside casing 10 and to the various portions of the semi-sausage casing 20 is effected by suitable heat and/or pressure sealing techniques.

Because the tear strip 30 is continous, one continuous motion, with one hand gripping the loose end 32 of the tear strip 30 and the other hand gripping the end 12 of the inside casing 10, enables the hygenic seal to be broken, and the semi-sausage casing 20 opened and removed to expose the lubricant insertion end 14 of the inside casing 10. The motion of pulling the tear strip 30 toward the closed end of the semi-sausage casing 20 pulls the semi-sausage casing 20 off over the lubricated insertion end 14 of the inside casing 10. The opening of the semi-sausage casing 20 along the indentation 24 thereby lessens any resistance to its removal.

The tear strip 30 is approximately one-half inch (1.3 cm) wide so that it can be easily gripped at its loose end 32. Also, the tear strip preferably is red in color so that it is clearly visible. Further, the tear strip is triple strength so that it will not fracture.

Figure 5:
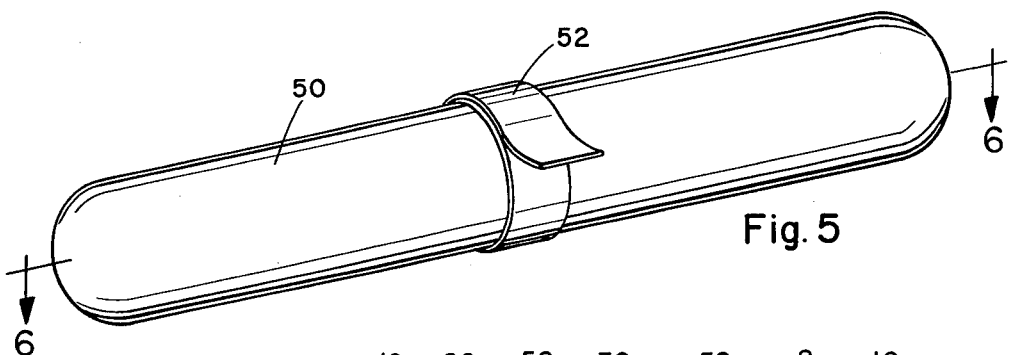
FIG. 5 is a perspective view of an outside casing enclosing the contraceptive device shown in FIG. 3.
Figure 6:
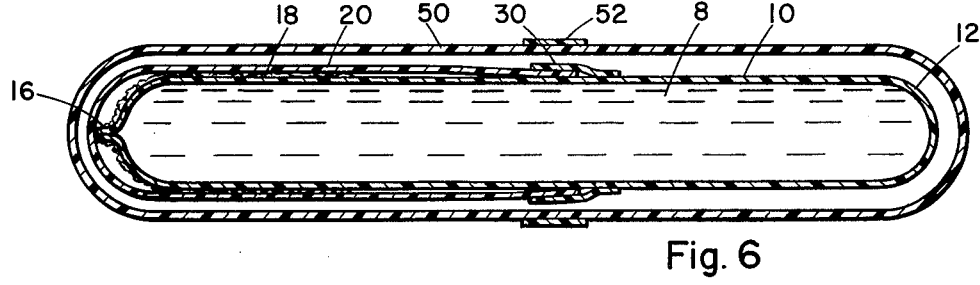
FIG. 6 is a sectional view taken on line 6—6 of FIG. 5.

For purposes of storage and transportation a sausage-shaped outside casing 50 (see FIG. 5) is provided to enclose the combination of the inside sausage casing 20 and semi-sausage casing 20 that is shown in FIG. 3. The outside casing 50 also may be made of sausage casing. The outside casing 50 is permanently sealed at both ends. A tear strip 52 is attached around the outside casing 50 so as to enable the outside casing to be opened in the same manner that an individually packaged cigar cellophane package is opened.

Having described my invention, I now claim.

1. A contraceptive device, comprising,
   a contraceptive gel having a pH of less than 3.0;
   a delicate elongated inside sausage casing containing the gel, and having a closed insertion end that will open to release the gel when the inside casing is squeezed;
   a lubricant covering the outside of the inside casing at said insertion end;
   a semi-sausage casing covering the lubricated insertion end of the inside casing for maintaining the lubricant in a lubricant state and at said insertion end, the semi-sausage casing having a closed end fitted over the lubricated insertion end of the inside casing and an open end fitted over the inside casing near the longitudinal mid-portion of the inside casing; and
   tear strip means having a first length removably attached to the semi-sausage casing near the open end of the semi-sausage casing and to the inside casing for hygenically sealing the lubricated insertion end of the inside casing and a second length attached to the semi-sausage casing to enable removal of the semi-sausage casing for exposing the lubricated insertion end of the inside sausage casing.

2. A contraceptive device according to claim 1, wherein the contraceptive gel consists of natural, edible, non-irritating, harmless ingredients.

3. A contraceptive device according to claim 2, wherein the contraceptive gel comprises,
   an acid for lowering the pH within the vagina to less than 4.0;
   an emollient lubricant;
   an emulsifier;
   means for stabilizing the gel;
   an aromatic deodorant;
   means for keeping the gel from liquefying at higher than ambient temperatures; and
   distilled water.

4. A contraceptive device according to claim 3, wherein the natural, edible, non-irritating, harmless ingredients comprise,
   citric acid for lowering the pH within the vagina to less than 4.0;
   glycerine for providing the emollient lubricant and the emulsifier;
   aromatic malic acid for stabilizing the gel and for providing the aromatic deodorant;
   kelco and/or wood celulose for keeping the gel from liquefying at higher ambient temperatures; and
   distilled water.

5. A contraceptive device according to claim 4, wherein the proportions of the ingredients are approximately
2 percent citric acid;
5 percent glycerine;
1 percent aromatic malic acid;
2 percent kelco and/or wood celulose; and
90 percent distilled water;
thereby providing a contraceptive gel having a stable pH of less than 3.0.

6. A contraceptive device according to claim 5, wherein the quantity of the contraceptive gel contained in the inside casing is approximately 1 to 3 ounces.

7. A contraceptive device according to claim 3, wherein the natural, edible, non-irritating, harmless ingredients comprise,
aromatic acetic acid for lowering the pH within the vagina to less than 4.0;
glycerine for providing the emollient lubricant and the emulsifier;
aromatic malic acid for stabilizing the gel and for providing the aromatic deodorant;
kelco and/or wood celulose for keeping the gel from liquifying at higher than ambient temperatures; and
distilled water.

8. A contraceptive device according to claim 1 further comprising, a sausage shaped outside casing for enclosing the inside casing, the semi-sausage casing and the tear strip means, and
a second tear strip means attached around the circumference of the outside casing for opening the outside casing.

9. A contraceptive device according to claim 1, wherein the tear strip is approximately ½ inch wide.

10. A contraceptive device according to claim 1, wherein the first and second portions of the tear strip are continuous.

11. The contraceptive device according to claim 1 wherein the tear strip is triple strength.

12. A contraceptive device according to claim 1, wherein the semi-sausage casing is weakened along an indentation extending from said open end to an area near its closed end where the tear strip is attached to the semi-sausage casing, and the tear strip is removably attached to the semi-sausage casing over the indentation so that when the tear strip is pulled toward the closed end, the semi-sausage casing will separate along the indentation.

13. A contraceptive device according to claim 12, wherein the tear strip extending over the indentation from the closed end of the semi-sausage casing is folded at the open end of the semi-sausage casing and wrapped around and removably attached to both the semi-sausage casing and the inside casing at the open end of the semi-sausage casing to hygenically seal the lubricated insertion end of the inside casing.

14. A contraceptive gel consisting of natural, edible, non-irritating, harmless ingredients comprising,
an acid for lowering the pH within the vagina to less than 4.0;
an emollient lubricant;
an emulsifier;
means for stabilizing the gel;
an aromatic deodorant;
means for keeping the gel from liquefying at higher than ambient temperatures; and
distilled water.

15. A contraceptive gel according to claim 14, wherein the natural, edible, non-irritating, harmless ingredients comprise;
citric acid for lowering the pH within the vagina to less than 4.0;
glycerine for providing the emollient lubricant and the emulsifier;
aromatic malic acid for stabilizing the gel and for providing the aromatic deodorant;
kelco and/or wood celulose for keeping the gel from liquefying at higher than ambient temperatures; and
distilled water.

16. A contraceptive gel according to claim 15, wherein the proportions of the ingredients are approximately
2 percent citric acid;
5 percent glycerine;
1 percent aromatic malic acid;
2 percent kelco and/or wood celulose; and
90 percent distilled water;
thereby providing a contraceptive gel having a pH of less than 3.0.

17. A contraceptive gel according to claim 14, wherein the natural, edible, non-irritating, harmless ingredients comprise,
aromatic acetic acid for lowering the pH within the vagina to less than 4.0;
glycerine for providing the emollient lubricant and the emulsifier;
aromatic malic acid for stabilizing the gel and for providing the aromatic deodorant;
kelco and/or wood celulose for keeping the gel from liquefying at higher than ambient temperatures; and
distilled water.

18. A contraceptive gel consisting of natural, edible, non-irritating ingredients comprising
an acid for lowering the pH of the vagina to less than 4.0;
an emollient lubricant;
an emulsifier;
means for stabilizing the gel;
an aromatic deodorant;
means for keeping the gel from liquifying at higher than ambient temperatures; and
distilled water;
thereby providing a contraceptive gel that is sufficiently harmless that it can be used in large enough dosages for maintaining contraception until after approximately 10 orgasms, or after the insertion of approximately 10 ounces of semen into the vagina.

19. A contraceptive device according to claim 1, wherein the semi-sausage casing is weakened along an indentation extending from said open end to an area near its closed end where the tear strip is permanently attached to the semi-sausage casing, and the tear strip is removably attached to the semi-sausage casing over the indentation so that when the tear strip is pulled toward the closed end, the semi-sausage casing will separate along the indentation and be automatically pulled off.

* * * * *

UNITED STATES PATENT AND TRADEMARK OFFICE
CERTIFICATE OF CORRECTION

PATENT NO. : 4,027,670
DATED : June 7, 1977
INVENTOR(S) : Emanuel H. Bronner

It is certified that error appears in the above-identified patent and that said Letters Patent are hereby corrected as shown below:

Column 1, Line 14, "contraception" should be --conception--.

Signed and Sealed this twenty-third Day of August 1977

[SEAL]

Attest:

RUTH C. MASON
*Attesting Officer*

C. MARSHALL DANN
*Commissioner of Patents and Trademarks*